(12) United States Patent
Lee et al.

(10) Patent No.: US 10,300,148 B2
(45) Date of Patent: May 28, 2019

(54) MESSENGER RNA NANOPARTICLES AND PREPARATION METHOD THEREFOR

(71) Applicant: UNIVERSITY OF SEOUL INDUSTRY COOPERATION FOUNDATION, Seoul (KR)

(72) Inventors: Jong-Bum Lee, Seoul (KR); Hye-Jin Kim, Seoul (KR)

(73) Assignee: UNIVERSITY OF SEOUL INDUSTRY COOPERATION, Seoul (KR)

( * ) Notice: Subject to any disclaimer, the term of this patent is extended or adjusted under 35 U.S.C. 154(b) by 0 days.

(21) Appl. No.: 15/514,889

(22) PCT Filed: Oct. 1, 2015

(86) PCT No.: PCT/KR2015/010405
§ 371 (c)(1),
(2) Date: Mar. 28, 2017

(87) PCT Pub. No.: WO2016/053033
PCT Pub. Date: Apr. 7, 2016

(65) Prior Publication Data
US 2017/0216457 A1    Aug. 3, 2017

(30) Foreign Application Priority Data

Oct. 2, 2014 (KR) .................. 10-2014-0133218

(51) Int. Cl.
*C12P 19/34* (2006.01)
*A61K 48/00* (2006.01)
(Continued)

(52) U.S. Cl.
CPC ............ *A61K 48/0066* (2013.01); *A61K 9/14* (2013.01); *A61K 48/0016* (2013.01);
(Continued)

(58) Field of Classification Search
None
See application file for complete search history.

(56) References Cited

U.S. PATENT DOCUMENTS

| 7,906,490 B2* | 3/2011 | Kool .................... C12N 15/113 514/44 A |
| 9,737,557 B2* | 8/2017 | Hammond ........... C12N 15/113 |

(Continued)

OTHER PUBLICATIONS

Wagner et al., Mechanism of Dimerization of Bicoid mRNA. The Journal of Biological Chemistry vol. 279, No. 6, Issue of Feb. 6, pp. 4560-4569, 2004. (Year: 2004).*

(Continued)

*Primary Examiner* — Christopher M Babic
*Assistant Examiner* — Arthur S Leonard
(74) *Attorney, Agent, or Firm* — Goldilocks ZONE IP Law (57) ABSTRACT

Disclosed are nanoparticles that are introduced into cells and express a specific protein and a manufacturing method thereof. More particularly, the present invention relates to mRNA nanoparticles, which increase the expression of a specific protein capable of stimulating the cellular immune system to induce cellular immune responses and are thus applicable to treat a variety of diseases, do not require passage across the nuclear envelope because a desired gene is delivered not as plasmid DNA itself but in the form of mRNA, thus improving the efficiency of protein expression, and the nanoparticles are generated through a one-step process with a relatively small amount of plasmid DNA via rolling circle transcription (RCT), thereby providing a simple and economical process for gene delivery. The present invention is also concerned with such mRNA nanoparticles.

3 Claims, 10 Drawing Sheets
(2 of 10 Drawing Sheet(s) Filed in Color)
Specification includes a Sequence Listing.

(51) Int. Cl.
    *B82B 1/00*     (2006.01)
    *A61K 9/14*     (2006.01)
    *C12N 15/63*     (2006.01)
    *C12N 15/87*     (2006.01)
    *B82Y 5/00*     (2011.01)

(52) U.S. Cl.
    CPC ............ *A61K 48/0091* (2013.01); *B82B 1/00* (2013.01); *C12N 15/63* (2013.01); *C12N 15/87* (2013.01); *C12P 19/34* (2013.01); *C12Y 207/07006* (2013.01); *B82Y 5/00* (2013.01)

(56) References Cited

U.S. PATENT DOCUMENTS

2007/0117109 A1*   5/2007   Rothemund ............ C12P 19/34
                                                                                                                435/6.12

2013/0156849 A1*   6/2013   de Fougerolles ...... A61K 48/00
                                                                                                                      424/450
2014/0187762 A1*   7/2014   Griffiths ............. C12N 15/1062
                                                                                                                      536/23.2

OTHER PUBLICATIONS

Jong Bum Lee et al., Self-assembled RNA interference microsponges for efficient siRNA delivery. Nat Mater. 2012; 11(4): 316-322 (Year: 2012).*

Neocles B. Leontis et al., Self-assembled RNA nanostructures, Insights /Perspectives, Aug. 15, 2014 , pp. 732-733, vol. 345 Issue 6198, Reserchgate.

Daehoon Han et al., Self-assembly of free-standing RNA membranes, Nature Communications, Jul. 4, 2014, pp. 1-7.

Office Action dated Aug. 18, 2016 of Korean Patent Application No. 10-2014-0133218, which corresponds to the above referenced application.

* cited by examiner

MESSENGER RNA NANOPARTICLES AND PREPARATION METHOD THEREFOR

STATEMENT REGARDING SPONSORED RESEARCH OR DEVELOPMENT

This invention was made with Korean Government support of Grant No. NRF-2016M3A9C6917402, awarded by the Bio & Medical Technology Development Program of the National Research Foundation of Korea, funded by the Korean Government.

CROSS-REFERENCE TO RELATED APPLICATIONS

This application claims the benefit under 35 U.S.C. section 371, of PCT International Application No.: PCT/KR2015/010405, filed on Oct. 1, 2015, which claims foreign priority to Korean Patent Application No.: KR10-2014-0133218, filed on Oct. 2, 2014, in the Korean Intellectual Property Office, both of which are hereby incorporated by reference in their entireties.

TECHNICAL FIELD

The present invention relates to nanoparticles that are introduced into cells and express a specific protein and a manufacturing method thereof. More particularly, the present invention relates to messenger RNA (mRNA) nanoparticles which consist of an mRNA that contains a repeated nucleotide sequence for expressing a specific protein, the nanoparticles being formed with the single-stranded mRNA, which is entangled and twisted. Such mRNA nanoparticles increase the expression of a specific protein capable of stimulating the cellular immune system to induce cellular immune responses and are thus applicable to the treatment of a variety of diseases. Also, the nanoparticles do not require passage across the nuclear envelope after transcription because a desired gene is delivered not as plasmid DNA itself but in the form of mRNA, thus improving the efficiency of protein expression. Further, the nanoparticles are safe and non-toxic in vivo because they are composed entirely of mRNA, which is a biomolecule, and are formed with mRNA strands that self-assemble into nanostructures, which confer resistance to nuclease degradation. Moreover, the nanoparticles are generated through a one-step process with a relatively small amount of plasmid DNA to produce RNA transcripts via rolling circle transcription (RCT), thereby providing a simple and economical process for gene delivery. The present invention is also concerned with a method of manufacturing such mRNA nanoparticles.

BACKGROUND ART

The expression of a desired protein by gene delivery depends on the cellular processes of DNA transcription and mRNA translation. The desired protein is typically selected from among proteins capable of stimulating the cellular immune system, and the increased protein expression induces cellular immune responses, thus providing therapeutic effects for various diseases. For this, many studies have been conducted for the delivery of plasmid DNA carrying genetic information. However, plasmid DNA has some barriers as follows. Once plasmid DNA enters cells, it must be transported to the nucleus where it can be transcribed into mRNA, and the resulting transcript needs to be exported from the nucleus into the cytoplasm to be translated into a target protein. This multistep process markedly reduces the effectiveness of gene expression, and moreover, plasmid DNA has low efficiency in penetrating through the nuclear envelope. Besides, there is the risk of genomic integration. Newly dividing cells during cell division are apt to contain the delivered exogenous DNA, which can alter the host cell's inherent genetic information. Thus, in order to overcome the problems associated with the delivery of plasmid DNA, many techniques have been developed including the employment of coating materials such as cationic polymers or lipids for particle formation, for example, as described in the following reference: R. Tachibana, H. Harashima, Y. Shinohara, H. Kiwada, Adv. Drug Delivery Rev. 2001, 52, 219-226.

However, another obstacle for DNA delivery is that most of the available organic and inorganic materials are foreign materials which, when taken up by cells, are recognized as foreign materials and thus potentially cause cytotoxicity.

DISCLOSURE

Technical Problem

Accordingly, the present invention has been made keeping in mind the above problems occurring in the related art, and it is, therefore, an object of the present invention to provide mRNA nanoparticles that overexpress a specific protein capable of stimulating the cellular immune system to induce cellular immune responses and are thus applicable to treat a variety of diseases, and a method of manufacturing such mRNA nanoparticles.

It is another object of the present invention to provide mRNA nanoparticles that do not require passage across the nuclear envelope after transcription because a desired gene is delivered not as plasmid DNA itself but in the form of mRNA, thus improving the efficiency of protein expression, and a method of manufacturing such mRNA nanoparticles.

It is a further object of the present invention to provide mRNA nanoparticles that are safe and non-toxic in vivo because they are composed entirely of mRNA, which is a biomolecule, and a method of manufacturing such mRNA nanoparticles.

It is yet another object of the present invention to provide mRNA nanoparticles that are famed by self-assembly, during which mRNA strands are entangled and twisted with each other into nanostructures, which confer resistance to nuclease RNase, and a method of manufacturing such mRNA nanoparticles.

It is still another object of the present invention to provide mRNA nanoparticles that are generated through a one-step process with a relatively small amount of plasmid DNA to produce RNA transcripts via rolling circle transcription (RCT), thereby providing a simple and economical process for gene delivery, and a method of manufacturing such mRNA nanoparticles.

Technical Solution

In order to accomplish the above described objects, the present invention is implemented in embodiments having the following constructions.

In one embodiment of the present invention, the mRNA nanoparticles according to the present invention comprise a repeated nucleotide sequence for expressing a specific protein.

In accordance with another embodiment of the present invention, the mRNA nanoparticles according to the present invention are characterized by having a spherical shape.

In accordance with a further embodiment of the present invention, the mRNA nanoparticles according to the present invention are characterized by having a diameter ranging from 30 to 200 nm.

In accordance with yet another embodiment of the present invention, the mRNA nanoparticles according to the present invention are formed with single-stranded mRNA strand that is entangled and twisted and thus are resistant to nuclease degradation.

In still another embodiment of the present invention, the method of manufacturing mRNA nanoparticles according to the present invention comprises the steps of preparing a DNA containing a nucleotide sequence encoding a specific protein; transcribing the DNA using an RNA polymerase to generate a single-stranded mRNA containing a repeated nucleotide sequence for expressing the specific protein; and allowing the single-stranded mRNA to self-assemble through entanglement and twisting to form the mRNA nanoparticles.

In accordance with still another embodiment of the present invention, the method of manufacturing mRNA nanoparticles according to the present invention is characterized in that the DNA is a circular double-stranded plasmid DNA.

In accordance with still another embodiment of the present invention, the method of manufacturing mRNA nanoparticles according to the present invention is characterized in that the DNA further comprises a nucleotide sequence encoding a promoter region for polymerization by an RNA polymerase and a ribosome-binding sequence.

In accordance with still another embodiment of the present invention, the method of manufacturing mRNA nanoparticles according to the present invention is characterized in that, at the DNA-preparing step, a circular double-stranded plasmid DNA is prepared and comprises, in sequence, a nucleotide sequence encoding a promoter region for polymerization by an RNA polymerase, a ribosome-binding sequence and a nucleotide sequence encoding a specific protein.

In accordance with still another embodiment of the present invention, the method of manufacturing mRNA nanoparticles according to the present invention is characterized in that the single-stranded mRNA is generated through rolling circle transcription.

In accordance with still another embodiment of the present invention, the method of manufacturing mRNA nanoparticles according to the present invention is characterized in that the plasmid DNA is used at a concentration of 1 to 5 nM.

Advantageous Effects

In accordance with exemplary embodiments of the present invention, the following effects may be obtained.

The present invention is applicable to treat a variety of diseases by enhancing the expression of a specific protein capable of stimulating the cellular immune system to induce cellular immune responses.

The present invention may also improve the efficiency of protein expression by bypassing the need for passage across the nuclear envelope after transcription because a desired gene is delivered not as plasmid DNA itself but in the form of mRNA.

Further, the present invention is safe and non-toxic in vivo because it is composed entirely of mRNA, which is a biomolecule.

Still further, the present invention has resistance to the nuclease RNase because nanoparticles are formed by self-assembly, during which mRNA strands are entangled and twisted with each other into nanostructures.

Moreover, the present invention provides a simple and economical process for gene delivery because nanoparticles are generated through a one-step process with a relatively small amount of plasmid DNA to produce RNA transcripts via rolling circle transcription (RCT).

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Hereinafter, a detailed description will be given of mRNA nanoparticles and a manufacturing method thereof according to the present invention, with reference to the appended drawings. Unless otherwise defined, all terms used herein have the same meaning as commonly understood by one of ordinary skill in the art to which the present invention belongs. If the meaning of the term used herein conflicts with the general meaning thereof, reference is to be made to the definition used herein. In the following description of the present invention, detailed descriptions of known constructions and functions incorporated herein will be omitted when they may make the gist of the present invention unclear. As used herein, when any part "comprises" or "contains" any element, it means that other elements are not precluded but may be further included, unless otherwise mentioned.

The present invention is directed to mRNA nanoparticles that are introduced into cells and overexpress a specific protein. The mRNA nanoparticles comprise a repeated nucleotide sequence for expressing a specific protein. Also, the mRNA nanoparticles have a constant shape and size and preferably have an overall spherical shape and a diameter ranging from 30 to 200 nm. The mRNA nanoparticles are famed with single-stranded mRNA strands that are entangled and twisted with each other. Since the protein which is overexpressed from the mRNA nanoparticles stimulates the cellular immune system and eventually induces cellular immune responses, the mRNA nanoparticles are able to treat a variety of diseases. Further, the mRNA nanoparticles are non-toxic in vivo because they are composed entirely of mRNA, which is a biomolecule. Moreover, since the mRNA nanoparticles can bypass the need for passage across the nuclear envelope for protein expression and are resistant to nuclease RNase, they may improve the efficiency of protein expression.

A method of manufacturing the above-described mRNA nanoparticles will be described in more detail below, and manufacturing is preferably conducted according to the method described below, without limitation thereto.

The method of manufacturing mRNA nanoparticles comprises the step of preparing a DNA that is a circular double-stranded plasmid DNA, which comprises, in sequence, a promoter to which an RNA polymerase binds to initiate transcription, a ribosome binding site (RBS) that allows ribosomes to bind onto the resulting mRNA transcript and a nucleotide sequence encoding a specific protein; the step of transcribing the plasmid DNA using an RNA polymerase to generate a long single-stranded mRNA containing a repeated nucleotide sequence for expressing the specific protein; and the step of allowing the single-stranded mRNA to self-assemble through entanglement and twisting to form the mRNA nanoparticles.

The DNA-preparing step serves to prepare a DNA containing a nucleotide sequence encoding a protein that is intended to be expressed. At this step, a circular double-stranded plasmid DNA is generated comprising a promoter region for polymerization by an RNA polymerase, a ribosome-binding sequence, and a nucleotide sequence encoding a specific protein (e.g. green fluorescent protein (GFP)). The plasmid DNA for expressing a specific protein is transcribed, and the resulting transcripts self-assemble into nanostructures, thus forming mRNA nanoparticles, which may be introduced into human cells to express the specific protein.

At the transcription step, a long single-stranded mRNA strand is generated from the plasmid DNA generated at the DNA-generating step via rolling circle transcription (RCT) using an RNA polymerase, the mRNA strand comprising a repeated nucleotide sequence for expressing a specific protein.

Figure 1:
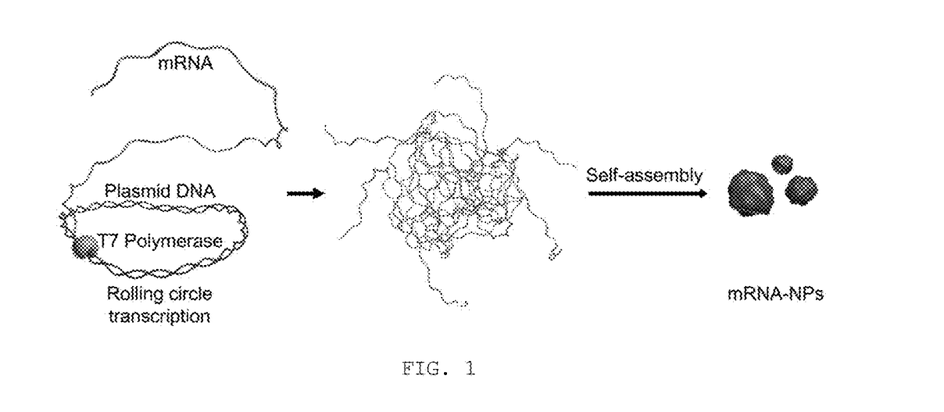
FIG. 1 is a schematic diagram showing the process of generating mRNA nanoparticles with plasmid DNA.

At the self-assembly step, the single-stranded mRNA strands self-assemble while being entangled and twisted with each other to form mRNA nanoparticles. At this step, the resulting nanoparticles become resistant to the nuclease RNase through the self-assembly process during which mRNA strands are entangled and twisted with each other. The mRNA nanoparticles containing genetic information for a desired protein have a diameter that may be controlled by changing the amount of plasmid DNA during the process of manufacturing mRNA nanoparticles. As described in detail below, when the plasmid DNA is mixed with an RNA polymerase and allowed to react at a predetermined temperature for a desired period of time, through the RCT reaction by the RNA polymerase are generated long single-stranded mRNA strands (see, FIG. 1), which self-assemble while being entangled and twisted with each other, thus producing mRNA nanoparticles. This one-step process via RCT provides a simple process for producing mRNA nanoparticles with a small amount of plasmid DNA.

MODE FOR INVENTION

A better understanding of the present invention may be obtained through the following examples which are set forth to illustrate, but are not to be construed to limit the present invention.

Example 1: Preparation of Plasmid DNA

A plasmid DNA as a template for RCT was designed so as to contain a nucleotide sequence (SEQ ID NO: 1) carrying genetic information for expressing a green fluorescent protein, a eukaryotic ribosomal binding sequence (RBS) (SEQ ID NO: 2), known as the Kozak sequence, and a nucleotide sequence (SEQ ID NO: 3) of a promoter region for T7 RNA polymerase, as follows.

<The nucleotide sequence of plasmid DNA>
CCCGTGTAAAACGACGGCCAGTTTATCTAGTCAGCTTGATTCTAGCTGA

TCGTGGACCGGAAGGTGAGCCAGTGAGTTGATTGCAGTCCAGTTACGCT

GGAGTCTGAGGCTCGTCCTGAATGATATGCGACCGCCGGAGGGTTGCGT

TTGAGACGGGCGACAGATCCAGTCGCGCTGCTCTCGTCGATCC-

CTATTTGTATAGTTCATCCATGCCATGTGTAATCCCAGCAGCTGTTACA

AACTCAAGAAGGACCATGTGGTCTCTCTTTTCGTTGGGATCTTTCGAAA

GGGCAGATTGTGTGGACAGGTAATGGTTGTCTGGTAAAAGGACAGGGCC

ATCGCCAATTGGAGTATTTTGTTGATAATGGTCTGCTAGTTGAACGCTT

CCATCTTCAATGTTGTGTCTAATTTTGAAGTTAACTTTGATTCCATTCT

TTTGTTTGTCTGCCATGATGTATACATTGTGTGAGTTATAGTTGTATTC

CAATTTGTGTCCAAGAATGTTTCCATCTTCTTTAAAATCAATACCTTTT

AACTCGATTCTATTAACAAGGGTATCACCTTCAAACTTGACTTCAGCAC

GTGTCTTGTAGTTCCCGTCATCTTTGAAAAATATAGTTCTTTCCTGTAC

ATAACCTTCGGGCA TGGCACTCTTGAAAAAGTCATGCCGTTTCATATG

ATCTGGGTATCTTGAAAAGCATTGAACACCATAAGAGAAAGTAGTGACA

AGTGTTGGCCATGGAACAGGTAGTTTTCCAGTAGTGCAAATAAATTTAA

GGGTAAGTTTTCCGTATGTTGCATCACCTTCACCCTCTCCACTGACAGA

AAATTTGTGCCCATTAACATCACCATCTAATTCAACAAGAATTGGGACA

ACTCCAGTGAAAAGTTCTTCTCCTTTACTCAT (SEQ ID NO: 1)-

CCATGGTGGC (SEQ ID NO: 2)-

ATCCCTATAGTGAGTCGTATTA (SEQ ID NO: 3)-
GGTGCGAGCGGATCGAGCAGTGTCGATCAGTTCTGGACGAGCGAGCTGT

CGTCCGACCCGTGATCTTACGGCATTATACGTATGATCGGTCCACGATC

AGCTAGATTATCTAGTCAGCTTGATGTCATAGCTGTTTCCTGAGGCTCA

ATACTGACCATTTAAATCATACCTGACCTCCATAGCAGAAAGTCAAAAG

CCTCCGACCGGAGGCTTTTGACTTGATCGGCACGTAAGAGGTTCCAACT

TTCACCATAATGAAATAAGATCACTACCGGGCGTATTTTTTGAGTTATC

GAGATTITCAGGAGCTAAGGAAGCTAAAATGAGTATTCAACATTTCCGT

GTCGCCCTTATTCCCTTTTTTGCGGCATTTTGCCTTCCTGTTTTTGCTC

ACCCAGAAACGCTGGTGAAAGTAAAAGATGCTGAAGATCAGTTGGGTGC

-continued
```
ACGAGTGGGTTACATCGAACTGGATCTCAACAGCGGTAAGATCCTTGAG

AGTTTACGCCCCGAAGAACGTTTTCCAATGATGAGCACTTTTAAAGTTC

TGCTATGTGGCGCGGTATTATCCCGTATTGACGCCGGGCAAGAGCAACT

CGGTCGCCGCATACACTATTCTCAGAATGACTTGGTTGAGTACTCACCA

GTCACAGAAAAGCATCTCACGGATGGCATGACAGTAAGAGAATTATGCA

GTGCTGCCATAACCATGAGTGATAACACTGCGGCCAACTTACTTCTGGC

AACGATCGGAGGACCGAAGGAGCTAACCGCTTTTTTGCACAACATGGGG

GATCATGTAACTCGCCTTGATCGTTGGGAACCGGAGCTGAATGAAGCCA

TACCAAACGACGAGCGTGACACCACGATGCCTGTAGCAATGGCAACAAC

GTTGCGCAAACTATTAACTGGCGAACTACTTACTCTAGCTTCCCGGCAA

CAATTAATAGACTGGATGGAGGCGGATAAAGTTGCAGGATCACTTCTGC

GCTCGGCCCTCCCGGCTGGCTGGTTTATTGCTGATAAATCTGGAGCCGG

TGAGCGTGGGTCTCGCGGTATCATTGCAGCACTGGGGCCAGATGGTAAG

CCCTCCCGCATCGTAGTTATCTACACGACGGGGAGTCAGGCAACTATGG

ATGAACGAAATAGACAGATCGCTGAGATAGGTGCCTCACTGATTAAGCA

TTGGTAATGAGGGCCCAAATGTAATCACCTGGCTCACCTTCGGGTGGGC

CTTTCTTGAGGACCTAAATGTAATCACCTGGCTCACCTTCGGGTGGGCC

TTTCTGCGTTGCTGGCGTTTTTCCATAGGCTCCGCCCCCTGACGAGCA

TCACAAAAATCGATGCTCAAGTCAGAGGTGGCGAAACCCGACAGGACTA

TAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGG

AAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGC

CCGACCGCTGCGCCTTATCCGGTAACTATCGTCTTGAGTCCAACCCGGT

AAGACACGACTTATCGCCACTGGCAGCAGCCACTGGTAACAGGATTAGC

AGAGCGAGGTATGTAGGCGGTGCTACAGAGTTCTTGAAGTGGTGGCCTA

ACTACGGCTACACTAGAAGAACAGTATTTGGTATCTGCGCTCTGCTGAA

GCCAGTTACCTCGGAAAAAGAGTTGGTAGCTCTTGATCCGGCAAACAAA

CCACCGCTGGTAGCGGTGGTTTTTTTGTTTGCAAGCAGCAGATTACGCG

CAGGATCTCAAGAAGATCCTTTGATTTTCTACCGAAGAAAGGCCCA
```

Example 2: Preparation of mRNA Nanoparticles 1 nM of the plasmid DNA prepared in Example 1 was mixed in a tube with 4 mM of Ribonucleotide Solution Mix (Bioline), Reaction buffer (8 mM Tris-HCl, 0.4 mM spermidine, 1.2 mM $MgCl_2$ and 2 mM dithiothreitol), and 50 units/ml of T7 RNA polymerase (New England Biolabs). The mixture was then incubated at 37° C. for 20 hrs to generate transcripts from the plasmid DNA via rolling circle transcription (RCT), thus yielding mRNA nanoparticles (hereinafter, referred to as 'mRNA-NPs').

Example 3: Evaluation for Size Distribution of mRNA Nanoparticles Transcribed from Various Concentrations of Plasmid DNA 1) mRNA nanoparticles were prepared according to the same procedure as in Example 2 with various concentrations (0.05 nM, 0.11 nM, 0.57 nM, 5.00 nM and 25.00 nM) of plasmid DNA.

Figure 2:
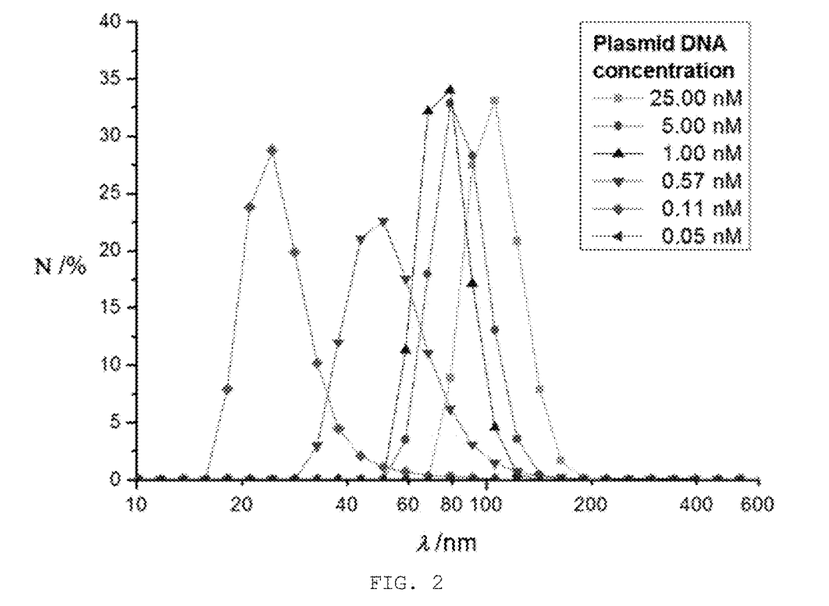
FIG. 2 is a graph showing the result of dynamic light scattering analysis for mRNA nanoparticles transcribed from various concentrations of plasmid DNA.

2) The mRNA nanoparticles prepared in Examples 2 and 3-1) were analyzed by dynamic light scattering analysis (Particle Size Analyzer WI30i), and the results are given in FIG. 2. Nanoparticles generated with 1 nM, 5 nM and 25 nM of plasmid DNA were also observed by scanning electron microscopy (SEM), and SEM images are given in FIG. 3.

Figure 3:
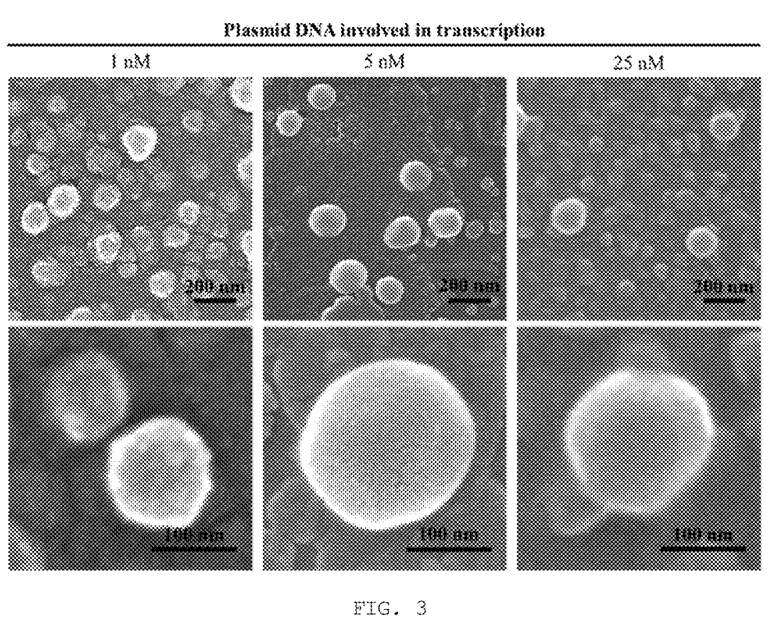
FIG. 3 shows SEM images of mRNA nanoparticles transcribed from various concentrations of plasmid DNA.

3) As shown in FIGS. 2 and 3, nanoparticles were not famed when the plasmid DNA was used at a concentration of 0.05 nM or less. Nanoparticles famed with 0.11 nM or more of plasmid DNA were found to have a diameter ranging from 30 to 200 nm while the diameter increased with increasing concentrations of plasmid DNA, but with plasmid DNA of higher than 5 nM, the diameter and particle number were not increased much further. It is an object of the present invention to produce nanoparticles with a minimal amount of plasmid DNA, and nanoparticles having a diameter of around 100 nm are preferable for cellular entry and pharmaceutical efficacy. For these reasons, the plasmid DNA may be preferably used at a concentration ranging from 1 to 5 nM.

Example 4: Evaluation for the Size and Shape of mRNA Nanoparticles

Figure 4:
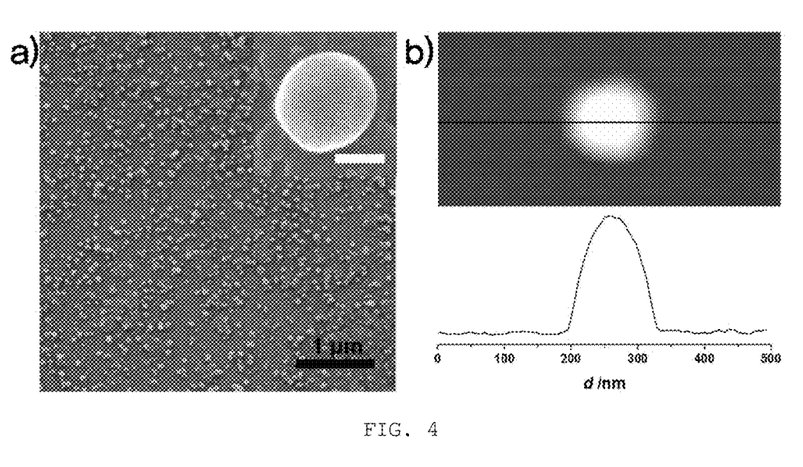
FIG. 4 shows microscopic images of mRNA nanoparticles according to one embodiment of the present invention.

The mRNA nanoparticles prepared with 5.00 nM of plasmid DNA in Example 3-1) were analyzed by scanning electron microscopy (SEM, XL30-FEG (ELI)) and atomic force microscopy (AFM, Park NX10 (Park Systems)). SEM and AFM images are given in FIGS. 4a and 4b, respectively. The SEM image (scale bar, 100 nm) showed that the mRNA-NPs had a spherical shape with a diameter ranging from 100 to 200 nm. Also, the spherical structure of the particles in the AFM image was correlated with the SEM result.

Example 5: Evaluation for the Component of mRNA Nanoparticles

1) Nanoparticles were prepared under the same conditions as in Example 2 except for the use of ribonucleotide solution mix containing Cyanine 3-labelled UTP (Enzo). Cyanine 3-UTP was used at concentrations of 5, 20 and 100 μM.

Figure 5:
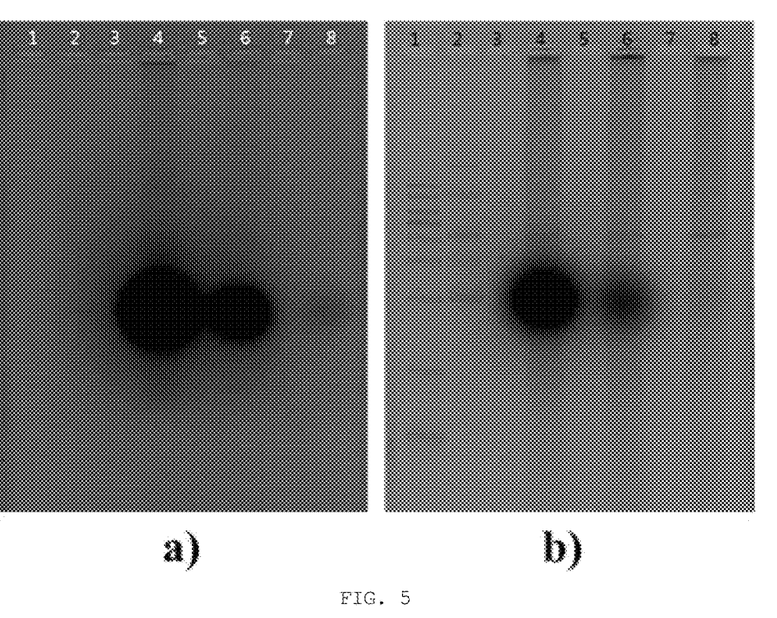
FIG. 5 shows the result of gel electrophoresis for identifying the component of mRNA nanoparticles.

2) The nanoparticles prepared in Example 5-1) were run on a 1.2 wt % agarose gel at 100V at room temperature in Tris-acetate-EDTA (TAE) buffer (40 mM Tris-acetate and 1 mM EDTA, pH 8.0, Biosesang), and the result is given in FIG. 5a. Also, the nanoparticles prepared in Example 5-1) were run after stained with Gelred on a 1.2 wt % agarose gel at 100V at room temperature in Tris-acetate-EDTA (TAE) buffer (40 mM Tris-acetate and 1 mM EDTA, pH 8.0, Biosesang). and the result is given in FIG. 5b. Lanes 1 and 2 indicate 1 kb DNA ladder marker and plasmid DNA, respectively. Lanes 3, 5 and 7 indicate samples not containing nanoparticles, and lanes 4, 6 and 8 indicate nanoparticle samples labeled with 100, 20 and 5 μM of Cyanine 3-UTP, respectively, which were prepared in Example 5-1).

Figure 6:
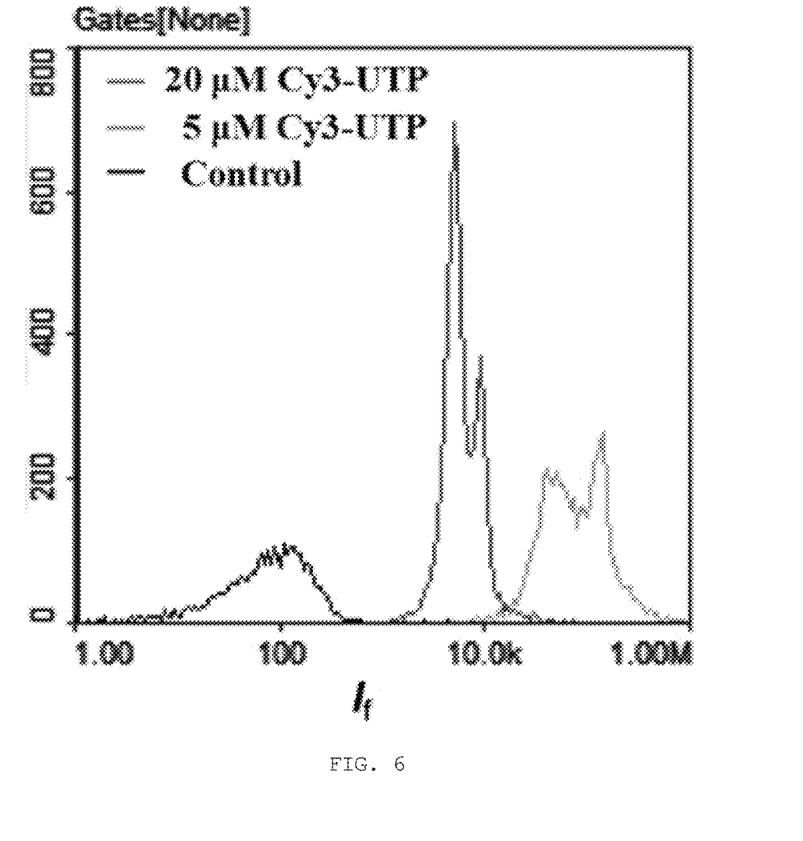
FIG. 6 shows the result of image cytometry for identifying the component of mRNA nanoparticles.

3) Image cytometry was also carried out for nanoparticles prepared according to the same procedure as in Example 5-1), and the result is given in FIG. 6. Cyanine 3-UTP (Cy3-UPT) was used at concentrations of 0 (control), 5 and 20 μM.

4) The nanoparticles could be labeled with Cy3-UTP, which emits orange fluorescence via the rolling circle transcription (RCT) reaction involving Cy3-UTP, and thus is readily visible under ultraviolet light. As shown in FIGS. 5a and 5b, the nanoparticles transcribed with Cy3-UTP were visible (see, lanes 4, 6 and 8), indicating that the nanoparticles were composed of RNA strands. Also, the image cytometry resulted in the finding that the nanoparticles showed strong fluorescence intensity and the intensity increased with increasing concentrations of Cy3-UTP (FIG. 6), indicating that the nanoparticles were composed of RNA strands.

Example 6: Evaluation for the Nuclease Resistance of mRNA Nanoparticles 50 ng of capped mRNA (1800 bp; hereinafter, referred to as 'Naked') containing a nucleotide sequence for expressing Xef-1 protein and 0.54 amole (12 μg) of mRNA nanoparticles (mRNA-NPs) were incubated with 2% and 10% fetal bovine serum (FBS, nuclease-containing) for 5 min and 1 hr at 37° C. Then, gel electrophoresis was performed on a 1% agarose gel, and the result is given in FIG. 7 (Control (cntl) not treated with FBS (lane 1); samples incubated with 2% FBS for 5 min (lane 2), 10% FBS for 5 min (lane 3), 2% FBS for 1 hr (lane 4) and 10% FBS for 1 hr (lane 5)).

Figure 7:
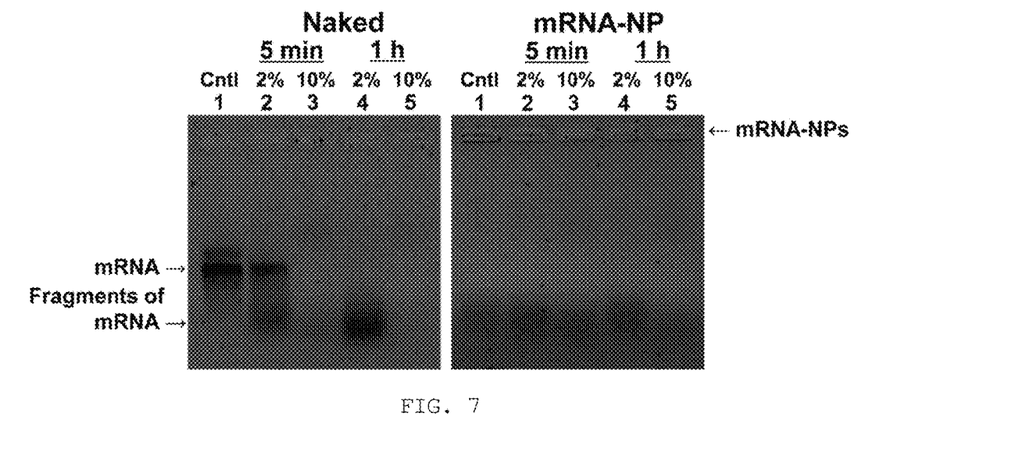
FIG. 7 shows the result of gel electrophoresis for evaluating nuclease resistance of mRNA nanoparticles.

2) As shown in FIG. 7, the long 'Naked' strand was rapidly degraded according to nuclease concentration and reaction time. In contrast, the mRNA-NPs, in which RNA strands were entangled and twisted with each other to form nanoparticles, were degraded to some extent but relatively large amounts thereof remained intact. These results indicate that the mRNA-NPs are resistant to nuclease degradation.

Example 7: Evaluation for Protein Expression from mRNA Nanoparticles

1) PC-3 cells were grown in RPMI 1640 (Welgene) supplemented with 10% fetal bovine serum (Gibco), 100 units/ml of penicillin, 100 μg/ml of streptomycin, and 1% antibiotic-antimycotic (Gibco) at 37° C. in a humidified atmosphere of 5% $CO_2$. 24 hrs before transfection, the cells were trypsinized, diluted with fresh medium ($3\times10^5$ cells/ml) and transferred to 24-well plates (500 μl per well).

2) The mRNA-NPs prepared in Example 2 were diluted with OPTI-MEMI (Gibco) and mixed with the transfection reagent TransIT-X2 (Mirus). The mixtures were then incubated at room temperature for 15 min to form a complex of mRNA-NPs with TransIT-X2.

3) Each concentration of mRNA-NPs after complexation was diluted and added to each well of cells, and the cells were then incubated at 37° C. for 3 to 48 hrs in a humidified atmosphere with 5% $CO_2$.

Figure 8:
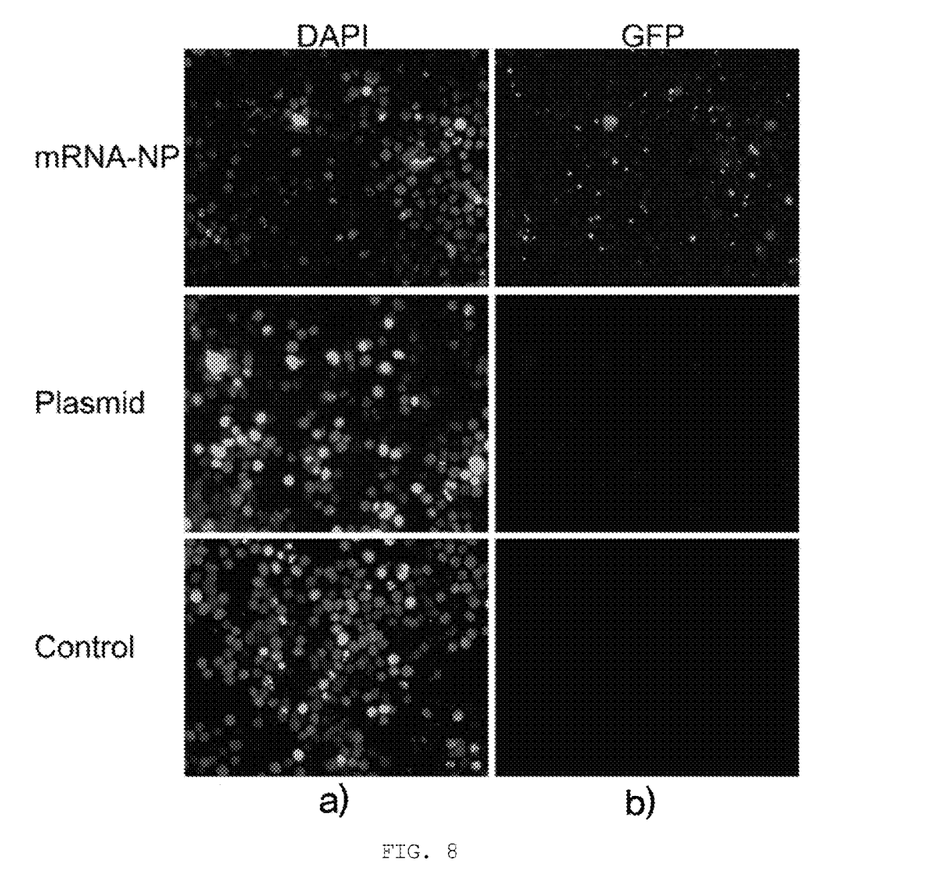
FIGS. 8 and 9 are fluorescent microscopic images for evaluating protein expression from mRNA nanoparticles.
Figure 9:
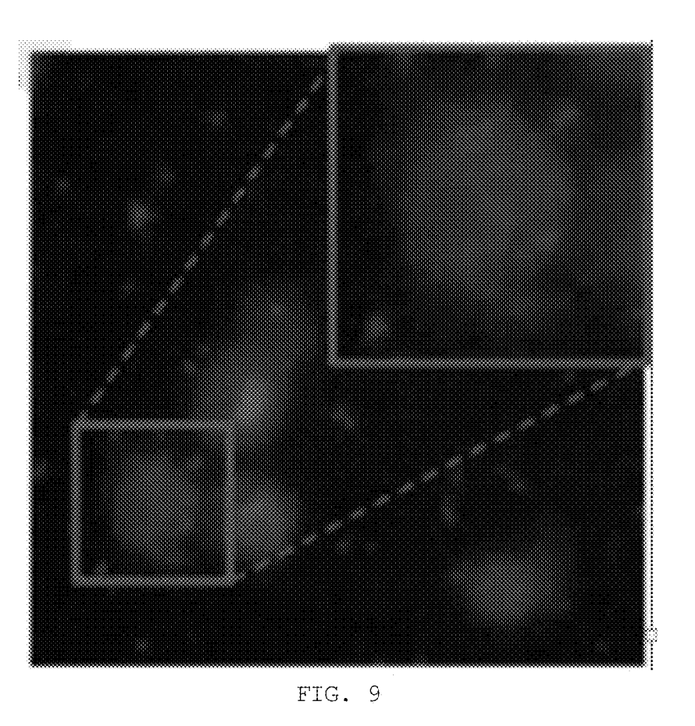

4) To image GFP-expressing PC-3 cells, the cells were grown on 8-well cell culture chamber slides (SPL Life Science). All the cells were fixed with 4% paraformaldehyde (MBiotech) and stained with DAPI at a concentration of 5 μg/ml to locate the cell nucleus. Fluorescent microscopy (Eclipse Ti (Nikon)) was carried out to image the transfected cells, and the results are given in FIGS. 8 and 9. FIG. 8 shows fluorescent microscopic images of the transfected PC-3 cells with different filters, where DAPI (blue) identifies the nuclear location (a) and the green signal indicates the expression of GFP protein (b). The cells were transfected with 0.6 fM of mRNA-NPs (top) transcribed from 1 nM of plasmid DNA, plasmid DNA (middle) of the same concentration as in the top, and neither mRNA-NPs nor plasmid DNA (control, bottom). FIG. 9 shows a merged DAPI and GFP image of the cells transfected with 0.1 fM of the mRNA-NPs generated with 5 nM of plasmid DNA.

5) As shown in FIG. 8, the mRNA-NPs-transfected PC-3 cells exhibited strong green fluorescence, indicating that GFP protein was produced in a large amount (top, mRNA-NPs). When cells were transfected with plasmid DNA, there was only relatively low green fluorescence, indicating that the GFP protein was produced in a small amount (middle, plasmid). As shown in FIG. 9, in mRNA-NPs-transfected PC-3 cells, the GFP protein (green) was found to be distributed around the nuclei (blue).

Figure 10:
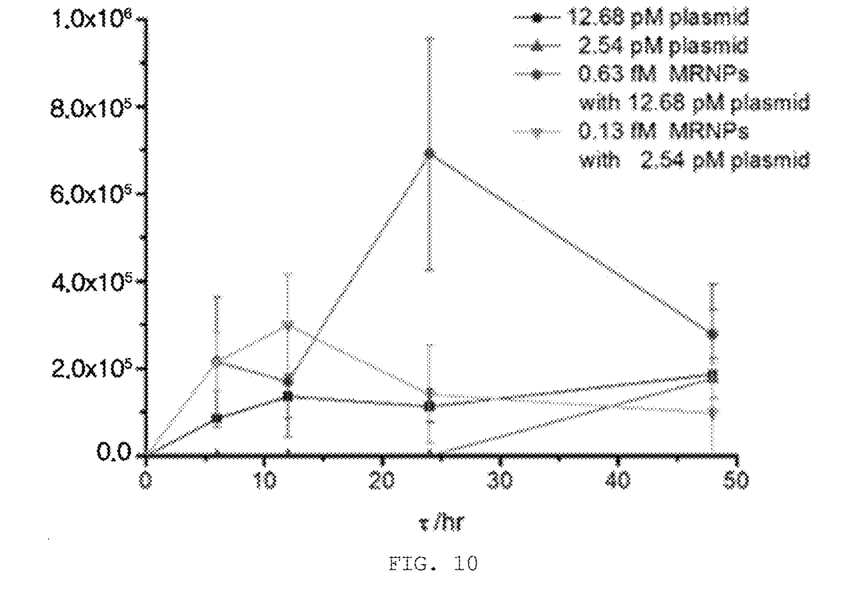
FIG. 10 is a graph showing the result of cytometry analysis for detecting protein expression from mRNA nanoparticles.

6) FIG. 10 is a graph showing the result of cytometry analysis. PC-3 cells were transfected with 0.6 fM (red) and 0.1 fM (orange) of mRNA-NPs. As controls, cells were transfected with 12 pM (navy) and 2 pM (green) of plasmid DNA. GFP fluorescence intensity and GFP expression duration varied with the samples. As shown in FIG. 10, the strongest GFP fluorescent intensity was observed 24 hrs post-transfection with 0.6 fM of mRNA-NPs, and the intensity was higher even after 40 hrs relative to the controls (see, red line). Taken together, as compared to the controls transfected with plasmid DNA, the mRNA-NPs gave stronger fluorescent intensities for a longer period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of manufacturing an mRNA nanoparticle comprising:
   preparing a DNA containing a nucleotide sequence encoding a specific protein;
   transcribing the DNA using an RNA polymerase to generate a single-stranded mRNA containing a repeated nucleotide sequence for expressing the specific protein; and
   allowing the single-stranded mRNA to self-assemble through entanglement and twisting to form the mRNA nanoparticle,
   wherein the DNA is a circular double-stranded plasmid DNA is used at a concentration ranging from 1 to 5 nM.

2. The method of claim 1, wherein the DNA further comprises a nucleotide sequence encoding a promoter region for polymerization by an RNA polymerase and a ribosome-binding sequence.

3. The method of claim 1, wherein the single-stranded mRNA is generated via rolling circle transcription.

* * * * *

SEQUENCE LISTING

```
<160> NUMBER OF SEQ ID NOS: 3

<210> SEQ ID NO 1
<211> LENGTH: 717
<212> TYPE: DNA
<213> ORGANISM: Artificial Sequence
<220> FEATURE:
<223> OTHER INFORMATION: region of plasmid DNA for protein generation

<400> SEQUENCE: 1
ctatttgtat agttcatcca tgccatgtgt aatcccagca gctgttacaa actcaagaag      60
gaccatgtgg tctctctttt cgttgggatc tttcgaaagg gcagattgtg tggacaggta     120
```

-continued

```
atggttgtct ggtaaaagga cagggccatc gccaattgga gtattttgtt gataatggtc      180
tgctagttga acgcttccat cttcaatgtt gtgtctaatt ttgaagttaa ctttgattcc      240
attcttttgt ttgtctgcca tgatgtatac attgtgtgag ttatagttgt attccaattt      300
gtgtccaaga atgtttccat cttctttaaa atcaatacct tttaactcga ttctattaac      360
aagggtatca ccttcaaact tgacttcagc acgtgtcttg tagttcccgt catctttgaa      420
aaatatagtt ctttcctgta cataaccttc gggcatggca ctcttgaaaa agtcatgccg      480
tttcatatga tctgggtatc ttgaaaagca ttgaacacca taagagaaag tagtgacaag      540
tgttggccat ggaacaggta gttttccagt agtgcaaata aatttaaggg taagttttcc      600
gtatgttgca tcaccttcac cctctccact gacagaaaat ttgtgcccat taacatcacc      660
atctaattca acaagaattg ggacaactcc agtgaaaagt tcttctcctt tactcat       717
```

<210> SEQ ID NO 2
<211> LENGTH: 10
<212> TYPE: DNA
<213> ORGANISM: Artificial Sequence
<220> FEATURE:
<223> OTHER INFORMATION: region of plasmid DNA for binding eukaryotic
      ribosomal

<400> SEQUENCE: 2
ccatggtggc                                                              10

<210> SEQ ID NO 3
<211> LENGTH: 22
<212> TYPE: DNA
<213> ORGANISM: Artificial Sequence
<220> FEATURE:
<223> OTHER INFORMATION: promoter region of plasmid DNA for RNA
      polymerase

<400> SEQUENCE: 3
atccctatag tgagtcgtat ta                                                22

UNITED STATES PATENT AND TRADEMARK OFFICE
CERTIFICATE OF CORRECTION

PATENT NO. : 10,300,148 B2
APPLICATION NO. : 15/514889
DATED : May 28, 2019
INVENTOR(S) : Lee et al.

Page 1 of 1

It is certified that error appears in the above-identified patent and that said Letters Patent is hereby corrected as shown below:

On the Title Page

Item (73) should read:
UNIVERSITY OF SEOUL INDUSTRY COOPERATION FOUNDATION

Signed and Sealed this
Third Day of September, 2019

Andrei Iancu
*Director of the United States Patent and Trademark Office*